(12) United States Patent
Varhol

(10) Patent No.: US 9,772,262 B1
(45) Date of Patent: *Sep. 26, 2017

(54) DIFFUSION SAMPLER

(71) Applicant: Bradley Varhol, Snellville, GA (US)

(72) Inventor: Bradley Varhol, Snellville, GA (US)

(73) Assignee: EON Products, Inc., Snellville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,783

(22) Filed: Oct. 7, 2016

Related U.S. Application Data

(63) Continuation-in-part of application No. 14/226,023, filed on Mar. 26, 2014, now Pat. No. 9,464,522.

(60) Provisional application No. 61/805,787, filed on Mar. 27, 2013.

(51) Int. Cl.
*G01N 1/10* (2006.01)
*E21B 49/08* (2006.01)
*G01N 33/18* (2006.01)

(52) U.S. Cl.
CPC ............. *G01N 1/10* (2013.01); *E21B 49/081* (2013.01); *E21B 49/083* (2013.01); *G01N 33/18* (2013.01)

(58) Field of Classification Search
CPC .......... G01N 1/10; E21B 49/08; E21B 49/081
See application file for complete search history.

(56) References Cited

U.S. PATENT DOCUMENTS

| 5,804,743 | A | 9/1998 | Vroblesky et al. |
| 9,464,522 | B2 * | 10/2016 | Varhol ............... E21B 49/08 |
| 2011/0061473 | A1 | 3/2011 | Paulsen et al. |

* cited by examiner

*Primary Examiner* — Paul West
(74) *Attorney, Agent, or Firm* — Bryan W. Bockhop; Bockhop Intellectual Property Law, LLC

(57) ABSTRACT

A diffusion sampler includes an elongated tubular structure, a first coupling device, at least a first membrane and a reservoir mechanism. The structure has an outer wall that defines an interior space therein. The outer wall defines a plurality of openings. A membrane is disposed around the outer wall at least in the area of the upper portion of the structure and is configured to allow at least one first selected type of molecule to pass therethrough. A reservoir mechanism is coupled to a bottom portion of the structure and is configured to define a reservoir in the lower portion of the structure that prevents a selected liquid from flowing out of the lower portion of the structure.

10 Claims, 5 Drawing Sheets

DIFFUSION SAMPLER

CROSS-REFERENCE TO RELATED APPLICATION(S)

This application is a continuation-in-part of U.S. patent application Ser. No. 14/226,023, filed Mar. 26, 2014, now issued as U.S. Pat. No. 9,464,522, the entirety of which is hereby incorporated herein by reference.

This application claims the benefit of U.S. Provisional Patent Application Ser. No. 61/805,787, filed Mar. 27, 2013, the entirety of which is hereby incorporated herein by reference.

BACKGROUND OF THE INVENTION

1. Field of the Invention

The present invention relates to liquid sampling devices and, more specifically, to a passive diffusion sampler.

2. Description of the Related Art

The efforts to provide for clean water and to prevent contamination of clean water sources require the ability to periodically monitor the quality of surface water and underground water (groundwater) sources for contaminants that may cause health hazards or violate law. Monitoring water quality typically involves obtaining a sample of the water from its place of residence and sending the sample to a laboratory for determination of the chemical make-up, including contaminant type and concentration. It is imperative that the method of sampling allow for a sample that represents the true water chemistry as it would be in-place and minimizes the effect of the sampling technique and the materials.

Frequently, groundwater samples are taken from a small diameter well installed through the soil or rock and intersecting the water that resides between the grains of soil or in the cracks in the rock at a depth of several feet to over a thousand feet. In these cases, the water must be lifted from the well in a manner that ensures the sample chemistry represents that of the intended sampling depth and the sampling method or device does not alter its chemistry. In some cases multiple zones at different vertical levels in the same well or surface water body must be sampled in such a way as to preserve the chemistry of the zone or discrete interval from which it is obtained. In the case of wells, the samples should be obtained with little or no suspended particulate materials, which is evidenced by turbidity. Likewise samples should not be over-exposed to air or be subjected to turbulence as these situations can cause the loss of volatile compounds that should be measured.

Because contamination spreads through water over time and can be conveyed from one location to another, it impacts the use of the land and the potential for liability from harm that may come from exposure to the contaminants. It is therefore necessary to repeatedly check the same locations on a regular and sometimes frequent basis. The cost of the water sampling process and subsequent analysis can have a negative impact on the industry or business deemed the responsible party and ongoing repetitive sampling to meet legal, health requirements, and land use requirements can multiply the cost exponentially.

Some existing systems use manually deployed and recovered "grab" samplers known as bailers or the use of specialized pumps that can provide mechanical lift and greater water volume. Grab samplers are containers, usually cylindrical and closed or with a valve at the bottom end, that are lowered into the fluid on a suspension cord or handle until submerged. The grab sampler fills and then is recovered with the sample inside. Pumps can be of several types, including: submersible pumps, which are lowered into the well and push water upwards, and peristaltic pumps, which sit at the surface with a suction tube into the fluid and which pull the fluid up through the tube and pump to be discharged. To ensure that samples obtained from wells using these methods represent the conditions of the water in the aquifer surrounding the well and not potentially "stagnant" water that resides in the well casing and that is not in contact with the water moving in aquifer itself, the process of "purging" is employed in which larger volume of water than is required for the sample is removed from the well before the sample is obtained. Purging most often involves three, or more, well volumes of water. Purging adds cost to the sampling event because it takes additional time and in some cases the purged water must be containerized and transported to an off-site location for disposal of contaminated materials. The time it takes to purge a well is determined by the capability of the equipment used, the physical characteristics of the well and of the aquifer. The action of purging is influenced by the individual user's techniques and results may vary in the same zone or results may not represent the intended sampling. In some cases, the combination of these several characteristics make well purging impractical or physically impossible. Whatever the device used, the liquid recovered is decanted into a laboratory sample bottle according to specific procedures, is sealed and taken to the lab.

Passive sampling has been employed to enable discrete interval sampling and to reduce the cost of sampling by eliminating well purging. Passive (also referred to as "no-purge sampling") involves deploying a device into the flow zone of the well (usually the area where the well-screen is located) or in open water. The sampler is left in place for a period of time and then recovered with a representative water sample enclosed. The amount of residence time is determined by the type of sampler and the ability for water of interest to be in contact with the sampler.

In passive diffusion sampling, a single semi-permeable membrane is formed into a container, usually tubular, filled with deionized water and sealed closed. The semi-permeable membrane is selected to allow certain molecules to pass or diffuse through the membrane when the device is placed in a fluid containing those molecules. When a diffusion sampler filled with deionized water is immersed in water having molecules of a type that will diffuse through the membrane, a concentration gradient for that compound will exist between the inside and outside of the membrane. The gradient will cause the molecules in the fluid with higher concentration to pass through the membrane to the fluid with lower concentration until the concentration on each side of the membrane is the same and then the concentration will maintain a dynamic equilibrium with the surrounding fluids. In this way, after sufficient time for diffusion has elapsed, the sample will represent the concentration of the compounds of interest in the fluid into which it is placed, as long as the membrane will allow for diffusion of that compound and the volume of fluid around the sampler is sufficiently large. Groundwater sampling using an appropriate and properly deployed passive diffusion method allows for a sample from a specific interval and screens out most suspended particles that may interfere with lab analysis.

Several types of membranes have been used for single membrane passive groundwater sampling, including:

Polyethylene because the samplers are inexpensive and work well for a range of compounds known as Volatile Organic Compounds (VOCs). Polyethylene membrane diffusion bag (PDB) samplers do not obtain samples of metals, semi-volatile compounds, or volatile compounds that are highly soluble, which together make up a substantial portion of the water sampling need. The method of using polyethylene based membranes for passive sampling is widely used and accepted for those volatile organic compounds that readily diffuse through the membrane.

Regenerated Cellulose Membrane Diffusion Samplers (RCMDS) allow diffusion of a wider range of compounds than Polyethylene membrane samplers. The membrane will allow diffusion of VOCs and some metals and some semi-volatile compounds. An inherent problem with RCMDs is that the cellulose material from which they are made is biodegradable making it susceptible to unpredictable field failure as the membrane is attacked by microorganisms causing it to become weak and then on occasion fail catastrophically, losing its sample contents before they can be used. The RCMD membranes are substantially more expensive than the PDB membranes, which reduces a second key benefit of the passive sampling technique.

Rigid Porous Polyethylene Diffusion samplers (RPPDs) consist of a short length (about 8-inches long) of small diameter porous polyethylene pipe that is filled with deionized water and sealed at each end. The pipe has a much thicker wall than the polyethylene membrane PDB samplers. The pipe has small pores that allow a hydraulic connection between the inside and outside of the sampler. RPPD samplers are typically suitable for some metals and semi-volatile compounds. However, they must be pressurized with deionized water to force the air out of the pores before use, making them inconvenient; they are usually not suitable for VOCs; the pores are typically sufficiently large that water molecules will pass through them under conditions of only a few inches of pressure or water head so that they only hold a small amount of sample without leaking and thus making it necessary to install multiple devices to obtain sufficient sample for most lab analysis; and they tend to be significantly more expensive than PDB or RCMD samplers.

Membrane Channel samplers use permanently installed pipe, sometimes with multiple vertical channels in which each channel is hydraulically connected to a single membrane at a specific depth. A pump for pumping the sample out of the channel is required. Pumps small enough to fit into the channels are not usually capable of recovering adequate sample volume from depth because of physical lift limitations. Additionally, when the water enters the membrane it will rise in the channel or "seek its own level" until the level is equal in the channel to the pressure head at the entry point outside the channel. The liquid in the channel becomes hydraulically isolated from the source and over time may not represent the water quality in the aquifer. And, once pumping begins the method ceases to be truly passive. The method is permanent and only has a single membrane per sample channel. Removing the sample from the chamber at depth can be difficult and may not be feasible in certain environments.

Hybrid Diffusion/Grab samplers (known by the brand name "Snap Sampler") operate using cylindrical collection bottles which have an orifice on each end of the cylinder. The device is submerged to the depth at which a sample is to be obtained and left in place for molecules to diffuse throughout the water in and out of the cylindrical bottles. When sufficient time has elapsed spring loaded caps are forced over the two orifice and the contents of the bottles are trapped and recovered. This method is unlike the membrane diffusion method and requires bulky and costly installation cables and triggers that will trigger the caps from the surface. On occasion the caps do not seal properly and/or the sample volume can be less than desirable.

Equilibrated Grab Samplers (known by the brand name "HydraSleeve") are narrow sleeves of polyethylene sealed at the bottom and with a valve mechanism at the top. The samplers are installed empty as a flat ribbon-like installation. After a suitable residence time for the surrounding well water to recover from the disturbance created by installation, the sampler is pulled at a rapid rate by its suspension cord. During the upward movement the sampler fills with water through the top valve, which seals capturing and isolating the sample within the device. These devices do not use a semi-permeable membrane to acquire the sample via diffusion but do rely on the natural diffusion of molecules through the well and aquifer to maintain representative concentrations in the zone where the sampler is activated. The performance and end result can be negatively affected by the user's actions during installation and activation and the samplers do not restrict silt and colloidal particles from entering the sampler.

Therefore, there is a need for a simple passive sampler that can take a liquid sample that remains undisturbed during the retrieval process.

SUMMARY OF THE INVENTION

The disadvantages of the prior art are overcome by the present invention which, in one aspect, is a diffusion sampler that includes an elongated tubular support structure, a top end cap, a bottom end cap, a first coupling device, at least a first membrane and a reservoir mechanism. The elongated tubular support structure has a top end, an opposite bottom end, and an outer wall that defines an interior space therein. The support structure includes an upper portion and a lower portion. A plurality of openings is defined by the outer wall of the support structure at least in an area of the upper portion. The top end cap is removably coupled to the top end of the support structure and is configured to be removable so as to allow a liquid (such as deionized water) to be poured into the support structure. The bottom end cap is removably coupled to the bottom end of the support structure and is configured to be removable so as to allow a liquid to be poured out of the support structure. The first coupling device is affixed to a selected one of the top end of the support structure and the top end cap, and is configured to couple the diffusion sampler to a cable. The first membrane is disposed around the outer wall at least in the area of the upper portion of the support structure. The first membrane is configured to allow at least one first selected type of molecule to pass therethrough. The reservoir mechanism is coupled to the bottom portion of the support structure and is configured to define a reservoir in the lower portion of the support structure that prevents a selected liquid from flowing out of the lower portion of the support structure.

The lower portion may include a material selected from a list consisting of: a rigid material; a flexible material; and a collapsible material. Also, the upper portion may include a material selected from a list consisting of: a rigid self-supporting membrane; a flexible tubular porous media; and rigid tubular porous media;

In another aspect, the invention is a diffusion sampling system that includes a tubular mesh, a first coupling device, a reservoir mechanism and at least one first membrane. The tubular mesh member has a bottom end and an opposite top end. The first coupling device is affixed to the tubular mesh member and is configured to couple the diffusion sampler to a cable. The reservoir mechanism holds a selected liquid in a bottom portion of the tubular mesh member. The first membrane is disposed around at least a portion of the tubular mesh member. The first membrane is configured to allow at least one selected molecule to pass therethrough.

In yet another aspect, the invention is a method of sampling a test liquid, in which a first membrane that allows transport therethrough of a first selected molecule is placed around an upper portion of a tubular support member. The upper portion defines a plurality of openings passing therethrough. The tubular support structure is placed in the test liquid for a predetermined amount of time. The tubular support structure is removed from the test liquid after the predetermined amount of time. The sample liquid is retrieved from the reservoir mechanism for subsequent analysis.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
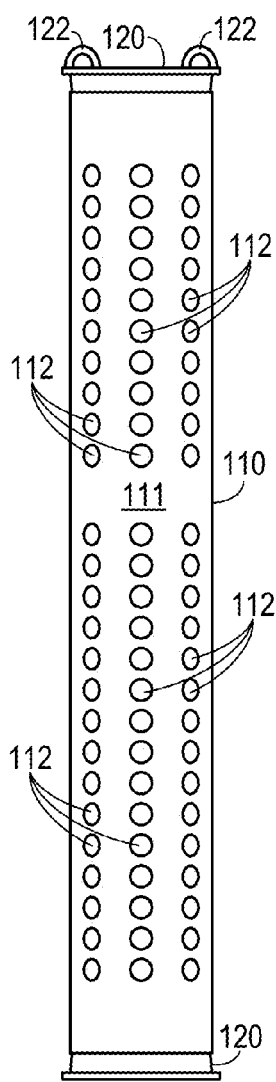
FIG. 1 is a schematic diagram of a first embodiment of a diffusion sampler support structure.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on." As used herein, a "membrane" is a selective barrier that allows the passage of certain constituents and retains other constituents found in a liquid. Examples of membranes include, but are not limited to, polymer membranes, fiber membranes, ceramic membranes, meshes, screens, etc. Also, as used herein, "tubular" includes an elongated three dimensional structure including an outer surface that defines an elongated volume therein; tubular structures can be, for example, cylindrical or prismatic.

As shown in FIG. 1, one embodiment of a diffusion sampler 100 employs a support structure 110 such as a tube 111 sealed at each end by end caps 120. A plurality of holes 112 pass through the tube so as to allow water (or other liquid being sampled) to flow freely into the tube. A couple of attachment rings 122 are attached to one or both of the end caps 120 and provide a coupling device for attachment of a line, such as a cable, for supporting the sampler in a sampling environment (such as in a well, a pond, a reservoir and the like).

The top end cap 120 can be removable to allow a sample liquid (such as deionized water) to be poured therein prior to the sampler 100 being placed in a test environment. The bottom end cap 120 can be removable to allow the sample liquid to be poured out of the sampler 100 into a receptacle after the sampler 100 has been exposed to the test liquid (e.g., groundwater in a well) for a sufficient amount of time. The end caps 120 do not need to be removable so long as there is a mechanism at, or near, the ends that allows for the sample liquid to be poured into the sampler 100 prior to the beginning of the sampling and to be drained out of the sampler 100 after the conclusion of the sampling.

Figure 2:
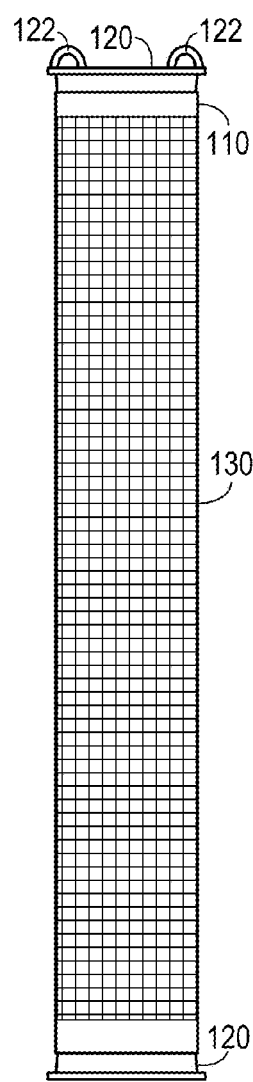
FIG. 2 is a schematic diagram of a second embodiment of a diffusion sampler support structure.
Figure 3:
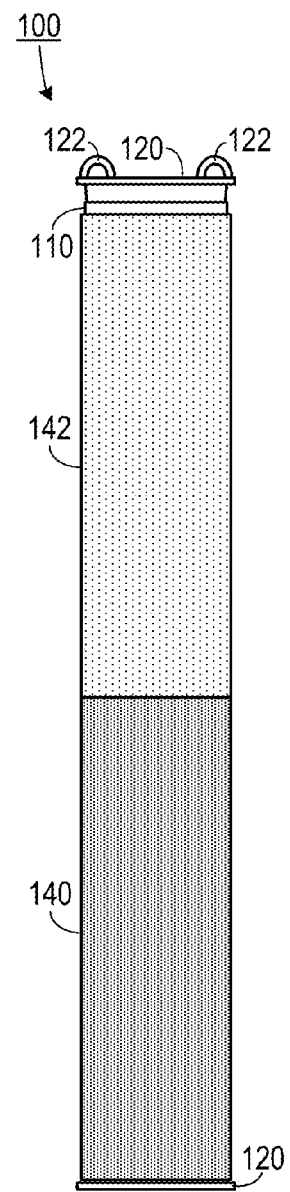
FIG. 3 is a schematic diagram of a diffusion sampler with a two membranes.

In another embodiment, as shown in FIG. 2, the support structure 110 can define a large open area covered by a mesh 130 that allows the free passage of liquid therein. As shown in FIG. 3, in both of the embodiments shown in FIGS. 1 and 2, a first membrane 140 and a second membrane 142, which is coaxial with the first membrane 140, are placed about the support structure 110. The first membrane 140 allows diffusion of predetermined molecules therethrough, but does not allow the liquid being sampled to flow therethrough, whereas the second membrane 142, which is placed above the first membrane 140, may allow the sampled liquid to flow freely therethrough. Thus, the first membrane 140 creates a reservoir that keeps the sampled liquid therein when the diffusion sampler 100 is removed from the sampling environment. In some embodiments, the first membrane 140 will allow diffusion of a first type of molecule therethrough and the second membrane 142 will allow diffusion of a second type of molecule therethrough.

Figure 4A:
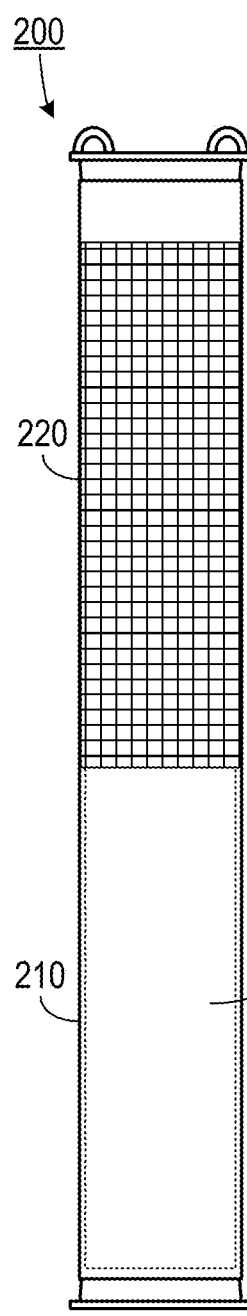
FIG. 4A is a schematic diagram of a third embodiment of a diffusion sampler support structure.
Figure 4B:
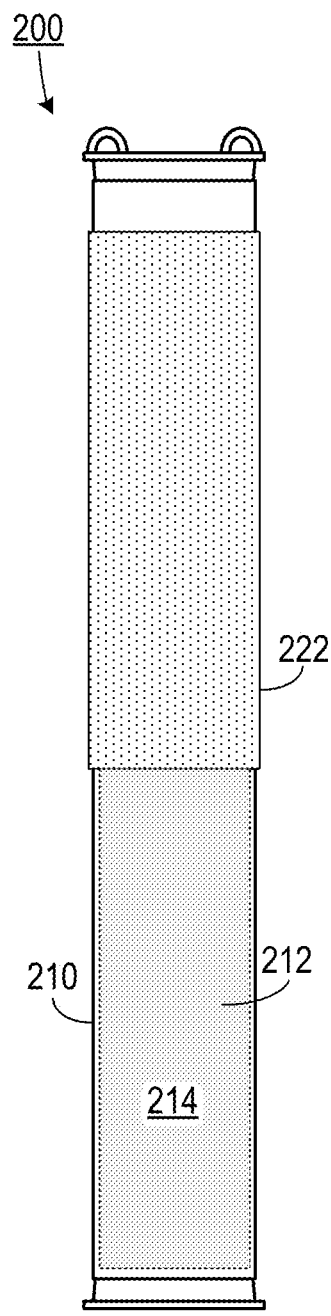
FIG. 4B is a schematic diagram of the embodiment shown in FIG. 4A with a membrane.

In one embodiment, the first membrane (lower portion) 140 can exist without a supporting tube and can be formed by a rigid material, a flexible material or a collapsible material. Also, the second membrane (upper portion) 142 can be a rigid self-supporting membrane, a flexible tubular porous media, or rigid tubular porous media;

In another embodiment, as shown in FIG. 4A, a diffusion sampler 200 can include a solid tube 210, that defines a reservoir 212 therein, and a substantially open area 220 disposed above the reservoir 212. The open area 220 can be covered with a mesh. As shown in FIG. 4B, a membrane 222 can cover the open area 220. The membrane may allow the flow of water 214 there through and/or can allow selected molecules to diffuse into the water 214.

Figure 5:
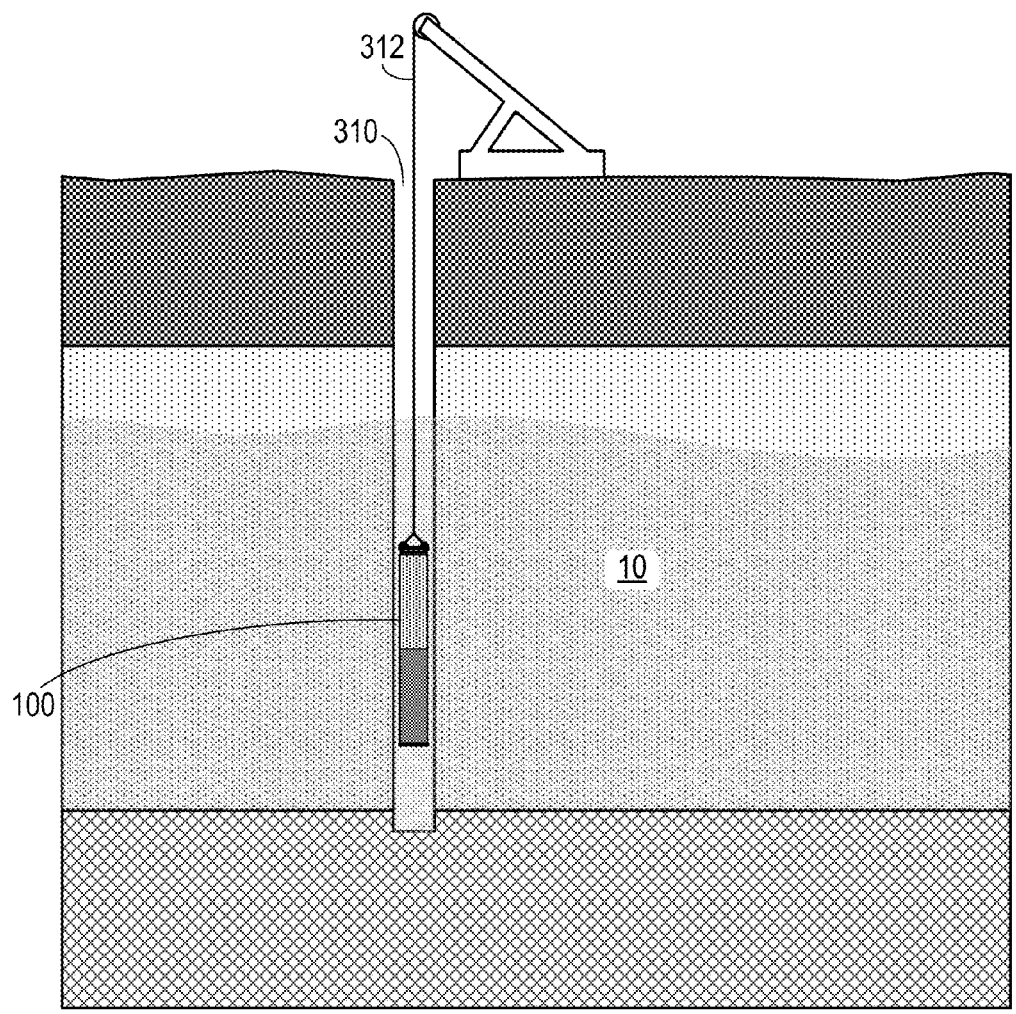
FIG. 5 is a schematic diagram of a diffusion sampler and support structure used in one representative application.

As shown in FIG. 5, a diffusion sampler 100, which has been filled with deionized water, is lowered into a sampling environment with a cable 312 (such as a chain, line, wire, rope, etc.). In the example shown, the diffusion sampler 100 is placed in a well 310 to sample groundwater 10. Typically, the sampler 100 is left in the sampling environment for a sufficient amount of time for the target molecule to diffuse into the reservoir and reach an equilibrium state with respect to the surrounding groundwater. The sampler 100 is then removed and the water in the reservoir is placed into a suitable container for further analysis at a lab.

Figure 6:
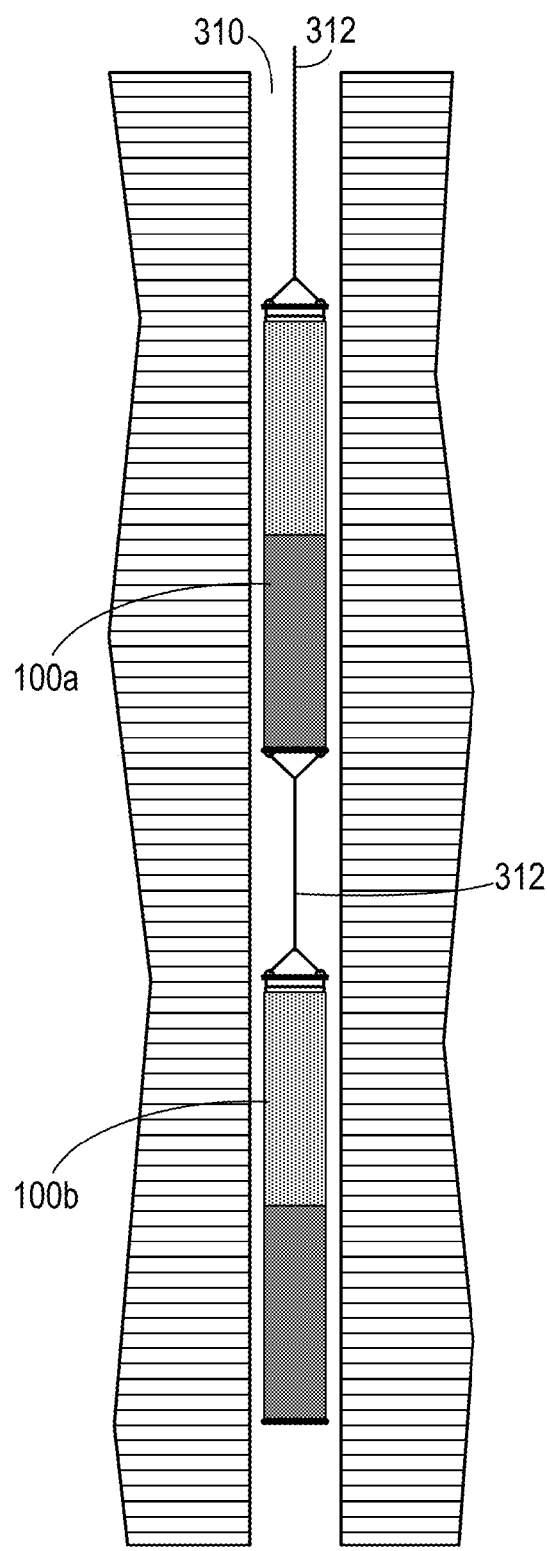
FIG. 6 is a schematic diagrams of two samplers connected in series in a well.

As shown in FIG. 6, two samplers 100a and 100b can be connected in series and suspended in a well 310 by a cable 310. This could be done to test liquid in different strata of the well 310 or to expand the number of types of membranes being used to test the liquid.

Figure 7:
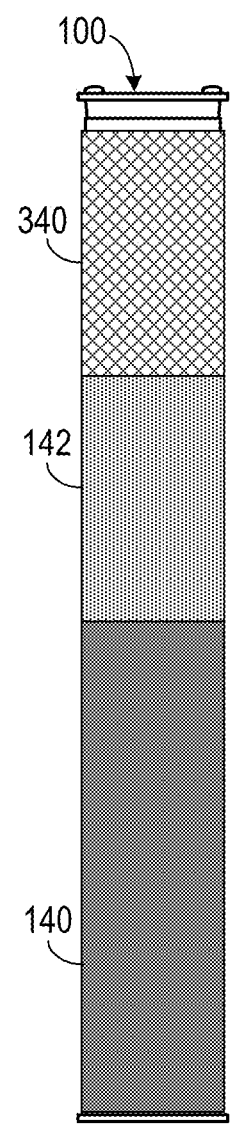
FIG. 7 is a schematic diagram of a sampler employing three membranes.

In one representative embodiment, two or more membranes of differing characteristics are employed on a single device in such a way that the molecules targeted by each membrane diffuse throughout a reservoir. The fluid in the reservoir represents the wider range of compounds that diffuse through each of the multiple membranes, better representing the surrounding water chemistry than any single membrane. The combination of multiple membranes and a reservoir are arranged in such a way as to take advantage of the benefits of various types of membranes while reducing the effects of the drawbacks of each membrane to produce inexpensively sufficient sample volume for laboratory analysis. This embodiment overcomes the inherent limitations of the existing samplers, which have a single membrane. It is a passive diffusion sampler that fulfills the need to reliably obtain a sufficient volume of representative samples of a wider range of compounds including VOCs, Semi-VOCs, Metals and additionally Anions and Cations from the intended zone, at a low cost. Also, as shown in FIG. 7, one sampler 100 can be fitted with a third membrane 340 so as to be able to target more types of molecules.

The samplers of this embodiment are based on the idea that two or more membranes can be used to construct a single inexpensive sampler in such a way that the benefits of each membrane are realized on a single device, without the drawbacks that occur when the membrane is used by itself. Integral to this method are the relative locations and length of the individual membranes along the body of the sampler, the reliance on the principal that molecules that enter a membrane in one location will diffuse through a liquid inside the reservoir, a support structure that prevents the membranes from collapsing and thereby retaining maximum sample volume in the device by limiting osmotic outflow of water from the certain membranes. Additionally, the optional use of a semi-permeable membrane as the reservoir will facilitate diffusion and provide for larger volumes of sample.

This embodiment allows a single, easy to use, sampler to be installed in water for a period of time. When it is removed, the contents will have adequate volume for most laboratory analysis. The contents will represent the surrounding water chemistry for compounds of interest and concentrations without purging and without the inherent risk of failure from biodegradation, or loss of liquid sample through membrane pores or membranes incompatible with the compounds of interest.

In one embodiment, a device includes two or more semi-permeable membranes or filters and a reservoir formed into a chamber which holds a fluid and into which fluid molecules of compounds present outside the chamber diffuse by passing through the pores of the membranes and further diffusing throughout the fluid in the chamber based on the known principle of molecular diffusion. Each membrane is formed into a chamber with an inside and an outside and with two opposite ends open, such that several membranes taken together can be aligned end to end to produce an assembly forming a single chamber such that there is single top, bottom, inside and outside to the single chamber. Nylon, Regenerated Cellulose, polyethylene, cellulose and other semi-permeable materials are often the materials of choice for the membranes.

A reservoir, which typically have about the same cross sectional size and shape as the membrane, assembly shape having the characteristic of holding water, is attached to the membrane assembly so as to extend linearly from one end of the assembly and thereby adding to the length of the membrane assembly and which provides an internal chamber or reservoir for the water and diffused compounds. The water holding reservoir is on the bottom of the assembly and the most permeable membranes are located above the reservoir. A variety of membranes and membrane combinations may be employed. A low density polyethylene is a membrane material may be suitable for the reservoir in one embodiment.

The construction is such that one single chamber is formed having an open fluid channel on the interior from one end (top) to the other end (bottom) by the combined membranes and reservoir placed end to end. As shown in FIGS. 6A-6B, an optional internal support structure may be used to reduce the ability for the chamber to becoming smaller by collapsing from loss of internal fluid under certain conditions. The internal support structure has openings between the structural members or perforations through a solid member that allow water passage from the outside of the structure to the inside of the structure. The membranes are attached to the support structure in a way that prevents the membranes from collapsing if the effects of osmosis are such that water would diffuse from the inside of the membrane to the outside.

In one embodiment, the support structure includes a tubular shape upon the external surface of which the membranes are fixed to form a tubular a tubular chamber The top of the device has a closure and the bottom of the device also has a closure. One of the two closures is left unsecured until the chamber is filled with fluid, which is typically de-ionized water, and then the closure is secured.

The exterior of the membranes are in direct contact with the liquid in which they are immersed. The interior sides of the membranes are in direct connection with the fluid in the chamber formed by the membrane. The membrane or filter pores form a pathway whereby certain molecules may pass from one side to the other of the membrane.

Figure 8:
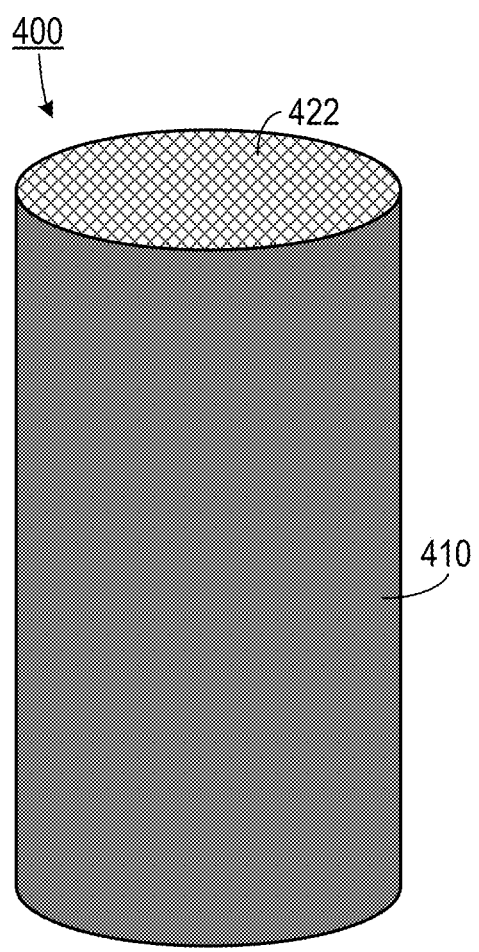
FIG. 8 is a schematic diagram of a sampler employing a top end membrane.

As shown in FIG. 8, one embodiment of a sampler 400 includes a reservoir portion 410 capped with a top membrane 422. The reservoir portion 410 could include a mesh with a membrane disposed about it or it could be a solid wall. Also, the bottom of the reservoir portion 410 could also be capped with a membrane.

In one alternate embodiment, an empty, collapsible reservoir having no internal fluid and having an upper portion comprising a support structure around which is fixed a membrane or an upper portion with a self-supporting rigid membrane or self-supporting porous media can be installed in a test fluid without filling the reservoir with a sample fluid prior to installation. After a predetermined amount of time, allowing for diffusion of molecules of the test fluid into the membrane or porous media, the sampler is removed from the surrounding liquid. As the sampler exits the fluid the weight of the fluid in the upper portion causes the fluid to transfer into the reservoir for retention until discharged into containers at the surface.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A diffusion sampler, comprising:
   (a) an elongated tubular support structure, having a top end and an opposite bottom end, and an outer wall that defines an interior space therein, the support structure including an upper portion and a lower portion, a plurality of openings defined by the outer wall of the support structure at least in an area of the upper portion, the lower portion including a material selected from a list consisting of: a rigid material; a flexible material; and a collapsible material, the upper portion including a material selected from a list consisting of: a rigid self-supporting membrane; a flexible tubular porous media; and a rigid tubular porous media;
   (b) a top end cap disposed at the top end of the support structure is configured to allow a liquid to be poured into the support structure;
   (c) a bottom end cap is disposed at the bottom end of the support structure and is configured to allow a liquid to be poured out of the support structure;
   (d) a first coupling device, affixed to a selected one of the top end of the support structure and the top end cap, that is configured to couple the diffusion sampler to a cable;
   (e) at least a first membrane disposed around the outer wall at least in the area of the upper portion of the support structure, the first membrane configured to allow at least one first selected type of molecule to pass therethrough; and
   (f) a reservoir mechanism, coupled to the bottom portion of the support structure, that is configured to define a reservoir in the lower portion of the support structure that prevents a selected liquid from flowing out of the lower portion of the support structure.

2. The diffusion sampler of claim 1, wherein the lower portion of the support structure comprises a plurality of openings passing therethrough and wherein the reservoir mechanism comprises a second membrane disposed about the outer wall in the area of the lower portion, the second membrane configured to allow at least one second selected type of molecule to flow therethrough, but configured to prevent the liquid from flowing out of the reservoir.

3. The diffusion sampler of claim 1, wherein the reservoir is formed as a result of the outer wall near the lower portion being solid without defining any openings passing therethrough.

4. The diffusion sampler of claim 1, wherein the outer wall at least in the area the upper portion of the support structure comprises a mesh.

5. The diffusion sampler of claim 1, wherein outer wall at least in the area the lower portion of the support structure comprises a mesh.

6. The diffusion sampler of claim 1, further comprising a second coupling device, affixed to a selected one of the bottom end of the support structure and the bottom end cap, that is configured to couple the diffusion sampler to a cable depending downwardly therefrom, thereby facilitating attachment of a second diffusion sampler in series to the diffusion sampler.

7. A method of sampling a test liquid, comprising the steps of:
   (a) placing a first membrane that allows transport therethrough of a first selected molecule around an upper portion of a tubular support structure, the upper portion defining a plurality of openings passing therethrough;
   (b) placing the tubular support structure, the membrane and a portion of a sample liquid in the test liquid for a predetermined amount of time;
   (c) removing the tubular support structure, the membrane and the portion of the sample liquid from the test liquid after the predetermined amount of time; and
   (d) retrieving the sample liquid for subsequent analysis.

8. The method of claim 7, further comprising the step of blocking flow of liquid out of the lower portion by placing a second membrane around the lower portion of the support structure, in which the lower portion defines a plurality of openings passing therethrough, wherein the second membrane is impervious to the sample liquid.

9. The method of claim 7, further comprising the step of blocking flow of liquid out of the lower portion by placing a solid tubular wall around the lower portion of the support structure.

10. The method of claim 7, wherein the step of retrieving the sample liquid from the reservoir mechanism comprises pouring the sample liquid from a bottom opening in the tubular support structure.

* * * * *